US008236811B2

(12) United States Patent
Bourrie et al.

(10) Patent No.: US 8,236,811 B2
(45) Date of Patent: Aug. 7, 2012

(54) THERAPEUTIC USE FOR TREATING OF LEUKEMIA

(75) Inventors: Bernard Bourrie, Paris (FR); Pierre Casellas, Paris (FR)

(73) Assignee: Sanofi, Paris (FR)

( * ) Notice: Subject to any disclaimer, the term of this patent is extended or adjusted under 35 U.S.C. 154(b) by 243 days.

(21) Appl. No.: 12/485,401

(22) Filed: Jun. 16, 2009

(65) Prior Publication Data

US 2009/0298790 A1    Dec. 3, 2009

Related U.S. Application Data

(63) Continuation of application No. PCT/FR2007/002171, filed on Dec. 27, 2007.

(30) Foreign Application Priority Data

Dec. 28, 2006    (FR) ...................................... 06 11492

(51) Int. Cl.
*A61K 31/519*    (2006.01)
(52) U.S. Cl. ..................... 514/264.11; 514/303; 514/362
(58) Field of Classification Search .................. None
See application file for complete search history.

(56) References Cited

U.S. PATENT DOCUMENTS

| | | | |
|---|---|---|---|
| 3,534,039 A | 10/1970 | Davoll | |
| 5,620,981 A | 4/1997 | Blankley et al. | |
| 5,733,913 A | 3/1998 | Blankley et al. | |
| 5,733,914 A | 3/1998 | Blankley et al. | |
| 5,952,342 A | 9/1999 | Blankley et al. | |
| 7,504,406 B2 | 3/2009 | Bourrie et al. | |
| 7,544,682 B2 | 6/2009 | Bourrie et al. | |
| 8,008,310 B2 * | 8/2011 | Bourrie et al. | 514/264.11 |
| 2008/0176874 A1 * | 7/2008 | Bourrie et al. | 514/264.1 |
| 2009/0048277 A1 | 2/2009 | Perreaut et al. | |
| 2009/0163522 A1 | 6/2009 | Bourrie et al. | |
| 2009/0233923 A1 | 9/2009 | Bourrie et al. | |

FOREIGN PATENT DOCUMENTS

| | | |
|---|---|---|
| EP | 0 790 997 B1 | 3/2000 |
| WO | WO 96/15128 | 5/1996 |
| WO | WO 96/34867 | 11/1996 |
| WO | WO 01/21577 A2 | 3/2001 |
| WO | WO 01/55147 | 8/2001 |
| WO | WO 01/70741 A1 | 9/2001 |
| WO | WO 02/12238 A2 | 2/2002 |
| WO | WO 03/000011 | 1/2003 |
| WO | WO 2004/063195 A1 | 7/2004 |
| WO | WO 2004/085436 | 10/2004 |
| WO | WO 2005/105097 A2 | 11/2005 |
| WO | WO 2006/007693 A1 | 1/2006 |
| WO | WO 2006/016067 A2 | 2/2006 |
| WO | WO 2007/003765 | 1/2007 |
| WO | WO 2007/080324 | 7/2007 |

OTHER PUBLICATIONS

Griesser, Chapter 8, The Importance of Solvates (pp. 211-233), Polymorphism: In the Pharmaceutical Industry, Hilfiker, 2006.*
Britain, <http://www.netlibrary.com/nlreader.dll?bookid=12783&filename=Page_126.html>, pp. 126-127, 2008.*
Berman et al. Blood, 1991, vol. 77, pp. 1666-1674.*
Yeh et al, Syntheses of 6-Amino-1,3-benzodioxin and Its p-Arylazo-Substituted Calix[4]arenes, J. Org. Chem., 1994 (59) pp. 754-757.
Alam, Fighting Cancer: 'Magic Bullets' on Target to Lead Market, Pharmalicensing.com (Mar. 8, 2005).
Anzali et al, 1. Endothelin antagonists: Search for Surrogates of Methylendioxyphenyl by Means of a Kohonen Neural Network, Bioorganic & Medicinal Chemistry Letters 8 (1998) pp. 11-16.
Ariza et al, Bocdene and Mocdene Derivatives of Catechols and Catecholamines, Organic Letters, 2001 (3) 9 pp. 1399-1401.
Asou et al, Establishment of a human acute myeloid leukemia cell line (Kasumi-1) with 8;21 chromosome translocation, Blood, 1991 (77) pp. 2031-2036.
Bennett et al, Proposals for the Classification of the Acute Leukaemias, Br J Haematol, 1976 (33) pp. 451-458.
Cambie et al, Towards the synthesis of aminodibenzo[b,e][1,4]dioxin derivatives via cationic ruthenium complexes, J. Organo. Chem., 1996 (507) pp. 1-21.
Carmichael et al, Evaluation of a Tetrazolium-based Semiautomated Colorimetric Assay: Assessment of Chemosensitivity Testing, Cancer Research, 1987 (47) pp. 936-942.
Cattan et al, A Comparison of a CB17scid mouse model and the tetrazolium-dye assay using human haematological tumour cell lines, Cancer Chemother Pharmacol., 1996 (38) pp. 548-552.
Chen et al, Establishment and Characterization of a Human Monocytoid Leukemia Cell Line, CTV-1, Gann, 1984 (75) pp. 660-664.
Clark et al, Synthesis and Analgesic Activity of 1,3-Dihydro-3-(substituted phenyl)imidazo[4,5-b]pyridin-2-ones and 3-(Substituted phenyl)-1,2,3-triazolo[4,5-b]pyridines, J. Med. Chem., 1978 (21) 9 pp. 965-978.
Colomb et al, Nuclear Texture Parameters as Discriminant Factors in Cell Cycle and Drug Sensitivity Studies, Cytometry, 1991 (12) pp. 15-25.
Drexler, Leukemia Cell Lines: in vitro Models for the Study of Chronic Myeloid Leukemia, Leukemia Research, 1994 (18) 12 pp. 919-927.
El Hadri et al, New Series of N-substituted Phenyl Ketone Oxime Ethers: Synthesis and Bovine Beta3-adrenergic Agonistic Activities, Pharmazie, 2003 (58) pp. 13-17.
Fujishita et al, Sensitivity of Non-Small-Cell Lung Cancer Cell Lines Established from Patients Treated with Prolonged Infusions of Paclitaxel, Oncology, 2003 (64) pp. 399-406.
Klutchko et al, 2-Substituted Aminopyrido[2,3-d]pyrimidin-7(8H)-ones. Structure-Activity Relationships Against Selected Tyrosine Kinases and in Vitro and in Vivo Anticancer Activity, J. Med. Chem., 1998 (41) pp. 3276-3292.
Koeffler et al, Acute Myelogenous Leukemia: A Human Cell Line Responsive to Colony-Stimulating Activity, Science, 1978 (200) pp. 1153-1154.

(Continued)

Primary Examiner — James D Anderson
(74) Attorney, Agent, or Firm — R. Brian McCaslin

(57) ABSTRACT

The disclosure relates to methods of treating leukaemia, in particular myeloid leukaemia, comprising administering the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea or a hydrate, a pharmaceutically acceptable salt or a solvate thereof.

10 Claims, No Drawings

OTHER PUBLICATIONS

Koeffler et al, An Undifferentiated Variant Derived From the Human Acute Myelogenous Leukemia Cell Line (KG-1), Blood, 1980 (56) 2 pp. 265-273.

Kuriyama et al, CLM-T1: A Cell Line Derived From T-Lymphocyte Acute Phase of Chronic Myelogenous Leukemia, Blood, 1989 (74) 4 pp. 1381-1387.

Lewell et al, Drug Rings Database with Web Interface. A Tool for Identifying Alternative Chemical Rings in Lead Discovery Programs, J. Med. Chem. 2003 (46) pp. 3257-3274.

Liang et al, Cryptophycins-309, 249 and other cryptophycin analogs: Preclinical efficacy studies with mouse and human tumors, Invest. New Drugs, 2005 (23) pp. 213-224.

Lozzio et al, Brief Communication: Cytotoxicity of a Factor Isolated From Human Spleen, J Natl Cancer Inst, 1973 (50) pp. 535-538.

Lozzio et al, Human Chronic Myelogenous Leukemia Cell-line with Positive Philadelphia Chromosome, Blood, 1975 (45) pp. 321-334.

Manley et al, Advances in the Structural Biology, Design and Clinical Development of Bcr-Abl Kinase Inhibitors for the Treatment of Chronic Myeloid Leukaemia, Biochimica et Biophysica Acta, 2005 (1754) pp. 3-13.

Mederski et al, 2. Endothelin Antagonists: Evaluation of 2,1,3-Benzothiadiazole as a Methylendioxyphenyl Bioisoster, Bioorganic & Medicinal Chemistry Letters 8 (1998) pp. 17-22.

Mirabelli et al, A Murine Model to Evaluate the Ability of in Vitro Clonogenic Assays to Predict the Response to Tumors in Vivo, Cancer Research, 1988 (48) 19 pp. 5447-5454.

Nakai et al, New Potent Antagonists of Leukotrienes C4 and D4. 1. Synthesis and Structure-Activity Relationships, J. Med. Chem., 1988 (31) pp. 84-91.

Palmer et al, Structure-activity Relationships for 2-anilino-6-phenylpyrido[2,3-d]pyrimidin-7(8H)-ones as Inhibitors of the Cellular Checkpoint Kinase Wee1, Bioorganic & Medicinal Chemistry Letters 15 (2005) pp. 1931-1935.

Plo et al, Influence of Ceramide Metabolism on P-Glycoprotein Function in Immature Acute Myeloid Leukemia KG1a Cells, Mol. Pharmacol., 2002 (62) pp. 304-312.

Saito et al, Establishment and Characterization of a new human eosinophilic leukemia cell line, Blood, 1985 (66) pp. 1233-1240.

Schroeder et al, Soluble 2-Substituted Aminopyrido[2,3-d]primidin-7-yl Ureas. Structure—Activity Relationships against Selected Tyrosine Kinases and Exploration of in Vitro and in Vivo Anticancer Activity, J. Med. Chem., 2001, 44, 1915-1926.

Sicinski, Killer Breast Cancer Therapy Hope, BBC News/Health Jan. 21, 2006.

Soda et al, Lymphoid Crisis with T-cell Phenotypes in a Patient with Philadelphia Chromosome Negative Chronic Myeloid Leukaemia, British Journal of Haematology, 1985 (59) pp. 671-679.

Thompson et al, Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receiptor-1 and Vascular Endothelial Growth Factor Receptor-2 Tyrosine Kinases, J. Med. Chem., 2005,48, 4628-4653.

Walsh, No 'Magic Bullet' Cure for Cancer, BBC News, International Version, Medical Notes, Feb. 1, 2007.

Westphal et al, Epidermal Growth Factor Receptors in the Human Glioblastoma Cell Line SF268 Differ From Those in Epidermoid Carcinoma Cell Line A431, Biochemical and Biophysical Research Comm., 1985 (132) 1 pp. 284-289.

Willard et al, Potential Diuretic—Beta-Adrenergic Blocking Agents: Synthesis of 3-[2[(1,1-Dimethytethyl) amino]-1-hydroxyethyl]-1,4-dioxino[2,3-g]quinolines, J. Org. Chem., 1981 (46) 19 pp. 3846-3852.

International Search Report for WO2008/102075A3 dated Aug. 28, 2008.

* cited by examiner

THERAPEUTIC USE FOR TREATING OF LEUKEMIA

This application is a continuation of International Application No. PCT/FR2007/002171, filed Dec. 27, 2007, which is incorporated herein by reference in its entirety; which claims the benefit of priority of French Patent Application No. 0611492, filed Dec. 28, 2006.

This invention relates to the treatment of leukemias, in particular myeloid leukemias.

Leukemia is a cancerous disease of the bone marrow and the blood. Four types of leukemia can be distinguished: chronic myeloid leukemia, acute myeloid leukemia, chronic lymphoid leukemia and acute lymphoid leukemia.

Myeloid leukaemias of the acute type with a rapid progression are called AML or acute myeloid leukemia. Myeloid leukaemias of the chronic type with a gradual, less aggressive progression are called CML or chronic myeloid leukemia. These are clonal diseases of the bone marrow characterized by a clonal expansion of myeloid cells which cannot differentiate normally and accumulate in the bone marrow and the blood.

According to a study by the American Cancer Society, it is estimated that 11,930 new cases of AML and 4,500 new cases of CML will be diagnosed in 2006 in the United States. Over the period from 2002 to 2006, the 5 year survival rate is 20.4% for AML and 42.3% for CML (Cancer Facts and Figures 2006, American Cancer Society, www.leukemia-lymphoma.org/).

According to the French-American-British (FAB) classification of 1976, there are 8 subtypes of AML, referred to as M0 to M7, depending on the type of cells from which the leukemia develops (Bennett et al, 1976, "Proposals for the classification of the acute leukaemias. French-American-British (FAB) co-operative group". *Br J Haematol* 33 (4): 451-8).

About 95% of patients suffering from CML bear a gene translocation between chromosomes 9 and 22 of the leukemic cells. This abnormality, known as Philadelphia chromosome (Ph1), causes proliferation and uncontrolled multiplication of all the types of white cells and platelets.

Currently, several drugs are available for the treatment of leukaemias. However, there remains a need for new active therapeutic compounds for the improvement of the strategies for treatment of patients suffering from leukemia or the development of a treatment alternative to the treatments already known (Plo et al, Mol Pharmacol, 2002, 62:304-312).

The product N-[2-(2,1,3-benzothiadiazol-5-ylamino)-6-(2,6-dichlorophenyl)pyrido[2,3-d]pyrimidin-7-yl]-N'-(1,1-dimethylethyl)-urea is described in the international application WO2007/003765. Its formula is shown below:

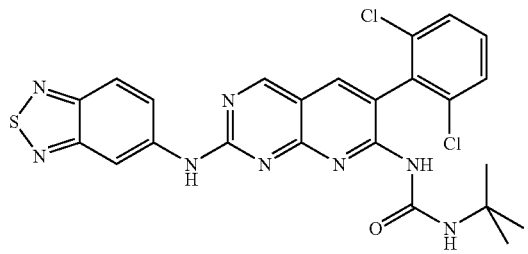

A process for preparation of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea is also described.

Although this compound can display a significant antitumor activity on cells in tests in vitro, new parameters such as the distribution of the compound in the tissues, the quantity of product in the serum, the pharmacokinetics and the metabolism are involved in the obtention of an effect in vivo, and not predictable on the basis of in vitro tests. It has moreover been demonstrated that in vitro antitumor activity is not always predictive of in vivo activity (Cancer Res. 1988 Oct. 1; 48(19): 5447-54, Cancer Chemother Pharmacol. 1996 38: 548-552).

By in vivo tests, it has been demonstrated that the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea displays significant in vivo anti-tumor activity in animals bearing human leukaemias.

An object of the present invention is the utilization of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea or a hydrate, a salt or a solvate thereof, for the preparation of a drug intended for the treatment of leukaemias. Leukaemia is understood to mean leukaemias such as chronic myeloid leukemia, acute myeloid leukemia, chronic lymphoid leukemia, acute lymphoid leukemia, and the various myeloproliferative syndromes.

In particular, the present invention relates to the utilization of the compound N-[2-(2,1,3-benzothiadiazol-5-ylamino)-6-(2,6-dichlorophenyl)pyrido-[2,3-d]pyrimidin-7-yl]-N'-(1,1-dimethylethyl)-urea, or a hydrate, a salt or a solvate thereof, for the preparation of a drug intended for the treatment of myeloid leukaemias. More particularly, the present invention relates to the utilization of the compound N-[2-(2,1,3-benzothiadiazol-5-ylamino)-6-(2,6-dichlorophenyl)pyrido-[2,3-d]pyrimidin-7-yl]-N'-(1,1-dimethylethyl)-urea, or a hydrate, a salt or a solvate thereof, for the preparation of a drug intended for the treatment of leukaemias of the AML type. More particularly, the present invention relates to the utilization of the compound N-[2-(2,1,3-benzothiadiazol-5-ylamino)-6-(2,6-dichlorophenyl)-pyrido[2,3-d]pyrimidin-7-yl]-N'-(1,1-dimethylethyl)-urea, or a hydrate, a salt or a solvate thereof, for the preparation of a drug intended for the treatment of leukaemias of the CML type.

An object of the present invention relates to the utilizations cited above for the treatment of mammals, in particular of man.

In the present invention, the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea can be administered to the animal tested by the oral route, the intravenous route, the intraperitoneal route or again by the intravenous route followed by an intraperitoneal route or again by the intravenous route followed by an oral route. In man, a conventional administration route is the intravenous route and/or the oral route.

One object of the present invention is the utilization of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea, or a hydrate, a salt or a solvate thereof, for the preparation of a drug intended for the treatment of leukaemias of the AML type where the drug is intended to be used by administration by the intravenous route.

One object of the present invention is the utilization of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea, or a hydrate, a salt or a solvate thereof, for the preparation of a drug intended for the treatment of leukaemias of the AML type where the drug is intended to be used by administration by the oral route.

One object of the present invention is the utilization of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea, or a hydrate, a salt or a solvate thereof, for the preparation of a drug intended for the treatment of leukaemias of the AML type where the drug is intended to be used by administration by the intravenous route and oral route.

One object of the present invention is the utilization of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea, or a hydrate, a salt or a solvate thereof, for the preparation of a drug intended for the treatment of leukaemias of the CML type where the drug is intended to be used by administration by the intravenous route.

One object of the present invention is the utilization of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea, or a hydrate, a salt or a solvate thereof, for the preparation of a drug intended for the treatment of leukaemias of the CML type where the drug is intended to be used by administration by the oral route.

One object of the present invention is the utilization of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea, or a hydrate, a salt or a solvate thereof, for the preparation of a drug intended for the treatment of leukaemias of the CML type where the drug is intended to be used by administration by the intravenous route and oral route.

In the present invention, the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea is typically formulated for administration in the form of a composition acceptable at the pharmaceutical level. These pharmaceutical compositions contain an effective dose of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea or a pharmaceutically acceptable salt, a hydrate or solvate of the said compound, as well as at least one pharmaceutically acceptable excipient.

The said excipients are selected depending on the desired pharmaceutical form and mode of administration, from the normal excipients which are known to the person skilled in the art.

In the pharmaceutical compositions of the present invention for oral or intravenous administration, the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea or possibly a salt, solvate or hydrate thereof can be administered to animals and to human beings in unit dosage form, mixed with conventional pharmaceutical excipients, for the prophylaxis or the treatment of the above disorders or diseases.

A PEG400 22%/Solutol 5%/G5 73% formulation is preferably used for the treatment by the intravenous route of mice bearing Kasumi1 tumors.

A Labrasol 21%/Solutol 5%/HCl 0.001N 74% formulation is preferably used for the treatment by the oral route of mice bearing Kasumi1 or KG1 tumors.

A PEG400 22%/Solutol 5%/G5 73% formulation is preferably used for the treatment by the intraperitoneal route of mice bearing EOL-1 tumors.

A PEG400 22%/Solutol 5%/G5 73% formulation is preferably used for the treatment, by the intravenous route followed by an intraperitoneal route, of mice bearing CTV1 tumors.

A DMSO 5%/Tween80 10%/$H_2O$ 85% formulation is preferably used for the treatment, by the oral route, or by the intravenous route followed by an intraperitoneal route, or again by the intravenous route followed by an oral route, of mice bearing KG1a tumors.

A DMSO 5%/Tween80 10%/$H_2O$ 85% formulation is preferably used for the treatment, by the intravenous route followed by an intraperitoneal route, of mice bearing K562 or CMLT1 tumors A DMSO 5%/Tween80 10%/$H_2O$ 85% formulation is preferably used for the treatment, by the intravenous route, of mice bearing KG1 tumors.

The appropriate unit dosage forms include forms by the oral route such as tablets, soft or hard gel capsules, powders, granules and oral solutions or suspensions and intravenous administration forms.

There may be special cases where higher or lower dosages are appropriate; such dosages do not fall outside the scope of the invention. According to the normal practice, the dosage appropriate for each patient is determined by the doctor depending on the mode of administration, and the weight and response of the said patient.

The therapy with the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea according to the present invention can be utilized at the same time as other therapies. In particular, the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea according to the invention can be administered in combination with one (or more) anti-cancer active principle(s), in particular antitumor compounds such as alkylating agents such as the alkylsulphonates (busulfan), dacarbazine, procarbazine, cloretazine, the nitrogen mustards (chlormethine, melphalan, chlorambucil, cyclophosphamide, ifosfamide), the nitrosoureas such as carmustine, lomustine, semustine, streptozocine and altretamine;

antineoplastic alkaloids such as vincristine, vinblastine, vinorelbine and vindesine;

taxanes such as paclitaxel or taxotere;

antineoplastic antibiotics such as actinomycin and bleomycin;

intercalating agents such as mitoxantrone;

antineoplastic antimetabolites: folate antagonists, methotrexate; inhibitors of purine synthesis; purine analogues such as mercaptopurine and 6-thioguanine; inhibitors of pyrimidine synthesis, aromatase inhibitors, capecitabine, pyrimidine analogues such as fluorouracil, gemcitabine, cytarabine and cytosine arabinoside; brequinar and nelarabine;

topoisomerase inhibitors such as irinotecan, exatecan, topotecan, teniposide, camptothecin or etoposide;

anticancer hormone agonists and antagonists including tamoxifen;

kinase inhibitors such as imatinib, nilotinib and dasatinib, midaustorin, sorafenib, lestaurtinib and tandutinib;

growth factor inhibitors;

antiinflammatories such as pentosan polysulphate, corticosteroids, prednisone and dexamethasone;

ceplene (histamine dihydrochloride);

anthracyclines such as daunorubicin, epirubicin, pirarubicin, idarubicin, zorubicin, aclarubicin, annamycin, doxorubicin, mitomycin and methramycin;

anticancer metal complexes, platinum complexes, cisplatin, carboplatin, oxaliplatin and satraplatin;

alpha interferon, triphenylthiophosphoramide;

antiangiogenic agents;

thalidomide;

farnesyl transferase inhibitors such as tipifarnib;

DNA methyl transferase inhibitors such as MG98;

immunotherapy adjuvants such as gemtuzumab ozogamicin and HuM 195;

biotherapeutic agents such as CT388-IL3;

antisense agents such as GTI-2040;

vaccines.

More particularly, the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea according to the invention can be administered in combination with one or more compound(s) of the anthracycline family.

More particularly, the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea according to the invention can be administered in combination with daunorubicin or in combination with cytosine arabinoside, or indeed in combination with daunorubicin and cytosine arabinoside.

According to the present invention, the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea can also be administered in combination with one or more other active principles useful in one of the pathologies mentioned above, for example an anti-emetic, analgesic, anti-inflammatory or anti-cachexia agent.

It is also possible to combine the compounds of the present invention with a radiation treatment.

These treatments can be administered simultaneously, separately, sequentially and/or spaced in time. The treatment will be adapted by the doctor depending on the patient to be treated.

In the present invention, the product N-[2-(2,1,3-benzothiadiazol-5-ylamino)-6-(2,6-dichlorophenyl)pyrido[2,3-d]pyrimidin-7-yl]-N'-(1,1-dimethylethyl)-urea is administered according to a dosage scheme which enables the treatment of leukaemias. The dosage scheme varies depending on the administration route and depending on the physical characteristics of the patient. The dosage schemes suitable for this purpose include those which display therapeutic efficacy for the treatment of disorders resulting from abnormal cellular proliferation. The product N-[2-(2,1,3-benzothiadiazol-5-ylamino)-6-(2,6-dichlorophenyl)pyrido[2,3-d]-pyrimidin-7-yl]-N'-(1,1-dimethylethyl)-urea can be administered as often as is necessary to obtain the therapeutic effect sought.

The efficacy of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea against leukaemias can be determined experimentally as in the following example which illustrates the invention.

EXAMPLE

Materials and Methods

Scid CB-17 mice (supplied by Charles River, Lyon, France) are used. At the time of the randomization, the animals have an average weight of 20-22 g and are aged from 6 to 9 weeks.

The animals are received at least one month before the experiment so as to allow perfect acclimatization. The health of the animals is examined the day before the implantation of the tumour and before the randomization so as to ensure that only animals in good health will be used for the experimental work. They are placed in type III macrolon cages with filtering hoods (maximum 8 mice per cage) in a sterile room where the air is continuously filtered to avoid all contamination. The sterility of the room is checked once a month. The cages are sterilized at 121° C. before use and changed twice a week. The temperature of the room is maintained at 22° C. and the relative humidity at 60+/−10%. The animals are placed in a natural light cycle condition. The water is sterilized at 121° C. for 30 minutes. The water consumption is followed visually each day, and the bottles are changed twice a week. Food and water are given ad libitum. The litter is sterilized at 121° C. for 30 minutes and changed twice a week.

The day before the first administration of a compound, the animals bearing tumors are classified into several groups. Only animals bearing two tumors which are palpable or of determined weight are selected and distributed at random into the treated groups and control groups. Each group is made up of 5 to 10 mice. At the start of the study, each cage is labeled with a card indicating the day of implantation of the tumour, the type of tumour, the compound tested and the mode of administration.

The implantation of the tumors is effected as follows: after removal of the tumour from the donor mouse, the tumour is cut up into fragments 2 to 3 mm in diameter, placed in a saline phosphate buffer, and implanted bilaterally with an adapted trocar.

Determination of Antitumor Activity

The volume of the tumors and its conversion into weight is estimated according to the formula: weight: (in mg)=$(a \times b^2)/2$, where a and b are respectively the length and the width of the tumour (mm). The tumors are measured twice a week with calipers. In the following tables, P indicates the weight of the tumors at the start of treatment.

Two parameters for estimation of antitumor activity are used: $\log_{10}$ of the cells killed (Log cell kill) and T/C.

Calculation of $\log_{10}$ of the cells killed=$(T-C)/3.32 \times Td$, where (T−C) is the delay in tumour growth and Td the volume (and weight) doubling time of the tumour (expressed in days). T is the median time in days for reaching a defined value (e.g. 1000 mg) in the treated group and C is the median time in days for reaching this same value in the control group. A value of $\log_{10}$ of the cells killed>0.7 is indicative of antitumor activity of the molecule. A value of $\log_{10}$ of the cells killed >2.8 is indicative of a very high antitumor activity of the molecule (J Liang et al, Invest New Drugs 2005; 23(3):213-24).

Calculation of T/C: the treated groups and the control groups are evaluated when the tumors of the control group reach approximately 1000 mg (median value of the group). The median weight of the tumors of each treated group is then determined. The T/C value ((weight of the tumors of the treated groups/weight of the tumors of the control groups)×100) in percent is an indication of the antitumor efficacy: a T/C value less than or equal to 42% is indicative of anti-tumour activity according to the American National Cancer Institute (NCI). A T/C value less than 10% is representative of very high anti-tumour activity.

The number of mice no longer displaying tumors a long time after the last administration (TFS=tumour-free survival), and considered as cured, can also constitute a parameter of activity of the molecule.

Evaluation of the toxicity of the compound tested: a weight loss greater than or equal to 20% or the appearance of any lethality in connection with the compound is considered as an excessively toxic treatment.

As examples, the results obtained with the compound N-[2-(2,1,3-benzothiadiazol-5-ylamino)-6-(2,6-dichlorophenyl)pyrido[2,3-d]pyrimidin-7-yl]-N'-(1,1-dimethyl-ethyl)-urea are given in the following Tables 1 to 7.

TABLE 1

Activity of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea in mice bearing KG1a tumors (AML)

| Formulation | P mg | Dose mg/kg/ injection | Route | Administration on days: | Total dose mg/kg | T/C at 22 days | Log$_{10}$ cells killed (TFS) |
|---|---|---|---|---|---|---|---|
| DMSO 5% Tween80 10% H$_2$O 85% | 91-98 | 17 | IV/IP | 5-13, 15/16, 18-20, 22, 24-26, 29, 31 | 340 | 0% | >>6 80% on day 120) |
| DMSO 5% Tween80 10% H$_2$O 85% | 147 | 40 × 2 (2 administrations per treatment day) | oral | 15-44 | 2400 | 14.9% | 3.0 |
| DMSO 5% Tween80 10% H$_2$O 85% | 1000 | 25/40 × 2 (2 oral administrations per treatment day) | IV/oral | 22-30/31-44 | 225/ 1120 | not relevant | >>6 |

IV/IP is understood to mean administration by the intravenous route followed by an intraperitoneal route; here the transition is effected between day 15 and day 16. IV/oral is understood to mean administration by the intravenous route followed by an oral route; here the transition is effected between day 30 and day 31. Treatment of tumors at the very advanced stage (1000 mg) by the IV route from days 22 to 30 at the dose of 25 mg/kg leads to a reduction in the tumour weight by 80%. On day 31, the compound is administered by the oral route until day 44. At the end of this second treatment period, the tumors are no longer measurable (<63 mg).

The cell line KG-1a (AML) is described by Koeffler et al., Blood 56: 265 (1980), and supplied by DSMZ ACC No. 421, Deutsche Sammlung von Mikroorganismen und Zellkulturen GmbH) Mascheroder Weg 1b, 38124 Brunswick, Germany).

TABLE 2

Activity of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea in mice bearing KG1 tumours (AML)

| Formulation | P mg | Dose mg/kg/ injection | Route | Administration on days: | Total dose mg/kg | T/C at 28 days | Log$_{10}$ cells killed (TFS) |
|---|---|---|---|---|---|---|---|
| DMSO 5% Tween80 10% H$_2$O 85% | 127-130 | 17 | IV | 19-28, 30, 32, 34, 36, 38 | 255 | 0% | >6 (100%) |
| Labrasol 21% Solutol 5% HCl 0.001N 74% | 130-132 | 40 × 2 (2 administrations per treatment day) | Oral | 18-24, 26, 28, 30, 32, 34, 36, 38, 40 | 1200 | 0% | 4.3 |

IV is understood to mean administration by the intravenous route.

The cell line KG-1 (AML) is described by Koeffler et al., Science 200: 1153-1154 (1978), and supplied by DSMZ ACC No. 14.

IV/IP is understood to mean administration by the intravenous route followed by an intraperitoneal route; here the transition is effected between day 26 and day 28.

TABLE 3

Activity of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea in mice bearing Kasumi1 tumours (AML)

| Formulation | P mg | Dose mg/kg/ injection | Route | Administration on days: | Total dose mg/kg | T/C at 28 days | $Log_{10}$ cells killed |
|---|---|---|---|---|---|---|---|
| PEG400 22% Solutol 5% G5 73% | 178 | 15 × 2 (Two administrations per treatment day) | IV | 25-31, 33, 34. (One single administration on day 30) | 255 | 20% | 3 |
| Labrasol 21% Solutol 5% HCl 0.001N 74% | 178 | 40 × 2 (Two administrations per treatment day) | oral | 25-31, 33, 34. (One single administration on day 30) | 680 | 17.5% | 2.4 |

IV is understood to mean administration by the intravenous route.

The cell line Kasumi-1 (AML) is described by Asou et al., Blood 77: 2031 (1991), and supplied by DSMZ ACC No. 220.

The cell line CTV1 (AML) is described by Chen et al., Gann 75: 660-664 (1984), and supplied by DSMZ ACC No. 40.

TABLE 4

Activity of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea in mice bearing EOL-1 tumours (AML)

| Formulation | P mg | Dose mg/kg/ injection | Route | Administration on days: | Total dose mg/kg | T/C at 14 days | $Log_{10}$ cells killed |
|---|---|---|---|---|---|---|---|
| PEG400 22% Solutol 5% G5 73% | 133-146 | 15 × 2 (2 administrations per treatment day) | IP | 8-10; 12-17; 19 | 300 | 5.7% | 3.1 |

IP is understood to mean administration by the intraperitoneal route.

The cell line EOL-1 (AML) is described by Saito et al., Blood 66: 1233-1240 (1985), and supplied by DSMZ ACC No. 386.

TABLE 5

Activity of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea in mice bearing CTV1 tumours (AML)

| Formulation | P mg | Dose mg/kg/ injection | Route | Administration on days: | Total dose mg/kg | T/C at 25 days | $Log_{10}$ cells killed |
|---|---|---|---|---|---|---|---|
| PEG400 22% Solutol 5% G5 73% | 100 | 25 | IV/IP | 17-23; 25-26/ 28-32 | 350 | 1.6% | 1.7 |

TABLE 6

Activity of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea in mice bearing K562 tumours (CML)

| Formulation | P mg | Dose mg/kg/ injection | Route | Administration on days: | Total dose mg/kg | T/C at 28 days | $Log_{10}$ cells killed (TFS) |
|---|---|---|---|---|---|---|---|
| DMSO 5% Tween80 10% $H_2O$ 85% | 63-80 | 25 | IV/IP | 4-11/ 12-25 | 550 | 0% | 4.2 (43% on day 130) |

IV/IP is understood to mean administration by the intravenous route followed by an intraperitoneal route; here the transition is effected between day 11 and day 12.

The cell line K-562 (CML) is described by Lozzio et al., J Natl Cancer Inst 50: 535 (1973) and by Lozzio et al., Blood 45: 321 (1975), and supplied by DSMZ ACC No. 10.

TABLE 7

Activity of the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea in mice bearing CMLT1 tumours (CML)

| Formulation | P mg | Dose mg/kg/injection | Route | Administration on days: | Total dose mg/kg | T/C at 22 days | Log$_{10}$ cells killed (TFS) |
|---|---|---|---|---|---|---|---|
| DMSO 5% Tween80 10% H$_2$O 85% | Palpable ~30 | 20 | IV/IP | 3-7/10-14; 17-21 | 300 | 1% | 1.5 (50% on day 42) |

IV/IP is understood to mean administration by the intravenous route followed by an intraperitoneal route; here the transition is effected between day 7 and day 10.

The cell line CMLT1 (CML) is described by Kuriyama et al. in Blood, 74: 1989, 1381-1387, by Soda et al. in British Journal of Haematology, 59: 1985, 671-679 and by Drexler, in Leukemia Research, 18: 1994, 919-927 and supplied by DSMZ ACC No. 7.

What is claimed is:

1. A method of treating leukemia in a patient comprising administering to said patient the compound N-[2-(2,1,3-benzothiadiazol-5-ylamino)-6-(2,6-dichlorophenyl)pyrido[2,3-d]pyrimidin-7-yl]-N'-(1,1-dimethylethyl)-urea or a pharmaceutically acceptable salt thereof, wherein the administration is a route selected from the group consisting of an intraperitoneal route, an intravenous route followed by an intraperitoneal route, and an intravenous route followed by an oral route, further comprising administering said compound in combination with daunorubicin.

2. The method according to claim 1 wherein the leukemia is selected from AML or CML.

3. A method of treating leukemia in a patient comprising administering to said patient the compound N-[2-(2,1,3-benzothiadiazol-5-ylamino)-6-(2,6-dichlorophenyl)pyrido[2,3]pyrimidin-7-yl]-N'-(1,1-dimethylethyl)-urea or a pharmaceutically acceptable salt thereof, wherein the administration is a route selected from the group consisting of an intraperitoneal route, an intravenous route followed by an intraperitoneal route, and an intravenous route followed by an oral route, further comprising administering said compound in combination with daunorubicin and cytosine arabinoside.

4. The method according to claim 3 wherein the leukemia is selected from AML or CML.

5. The method of claim 1, wherein the administration route is intraperitoneal.

6. The method of claim 1, wherein the administration route is intravenous followed by an intraperitoneal route.

7. The method of claim 1, wherein the administration route is intravenous followed by an oral route.

8. The method of claim 3, wherein the administration route is intraperitoneal.

9. The method of claim 3, wherein the administration route is intravenous followed by an intraperitoneal route.

10. The method of claim 3, wherein the administration route is intravenous followed by an oral route.

* * * * *

UNITED STATES PATENT AND TRADEMARK OFFICE
CERTIFICATE OF CORRECTION

PATENT NO.         : 8,236,811 B2
APPLICATION NO.    : 12/485401
DATED              : August 7, 2012
INVENTOR(S)        : Bernard Bourrie et al.

Page 1 of 1

It is certified that error appears in the above-identified patent and that said Letters Patent is hereby corrected as shown below:

On the title page, in field (56), in column 2, under "Other Publications", line 9, delete "Methylendioxyphenyl" and insert -- Methylenedioxyphenyl --, therefor.

On page 2, in column 1, under "Other Publications", line 22, delete "Methylendioxyphenyl" and insert -- Methylenedioxyphenyl --, therefor.

On page 2, in column 2, under "Other Publications", line 18, delete "Receiptor-1" and insert -- Receptor-1 --, therefor.

On page 2, in column 2, under "Other Publications", line 27, delete "Dimethytethyl" and insert -- Dimethylethyl --, therefor.

In column 4, line 62, delete "methramycin;" and insert -- mithramycin; --, therefor.

In column 5, line 64, delete "macrolon" and insert -- makrolon --, therefor.

In column 12, line 16, in claim 3, delete "[2,3]" and insert -- [2,3-d] --, therefor.

Signed and Sealed this
Twelfth Day of March, 2013

Teresa Stanek Rea
*Acting Director of the United States Patent and Trademark Office*